United States Patent [19]

Stauffer

[11] Patent Number: 4,990,696
[45] Date of Patent: Feb. 5, 1991

[54] METHYL ALCOHOL PROCESS

[76] Inventor: John E. Stauffer, 6 Pecksland Rd., Greenwich, Conn. 06831

[21] Appl. No.: 530,033

[22] Filed: May 29, 1990

Related U.S. Application Data

[63] Continuation-in-part of Ser. No. 297,298, Jan. 13, 1989, which is a continuation-in-part of Ser. No. 40,839, Apr. 20, 1987, abandoned, which is a continuation-in-part of Ser. No. 793,534, Oct. 31, 1985, abandoned.

[51] Int. Cl.[5] .................... C07C 29/124; C07C 31/04; C07C 17/10; C07C 17/158
[52] U.S. Cl. .................................. 568/893; 570/241; 570/261; 570/224
[58] Field of Search .......................................... 568/893

[56] References Cited

U.S. PATENT DOCUMENTS

| | | | |
|---|---|---|---|
| 1,688,726 | 10/1928 | McKee | 568/893 |
| 2,447,410 | 8/1948 | Hampel | 570/220 |
| 2,547,139 | 4/1951 | Randall | 200/660 |
| 3,172,915 | 3/1965 | Borkowski et al. | 508/893 |
| 3,420,901 | 1/1969 | Schulz | 570/243 |
| 3,642,918 | 2/1972 | Buhl et al. | 570/224 |
| 4,192,822 | 3/1980 | Sweeney et al. | 570/261 |
| 4,523,040 | 6/1985 | Olah | 508/893 |

FOREIGN PATENT DOCUMENTS 1468781  5/1969  Fed. Rep. of Germany ...... 568/893

Primary Examiner—J. E. Evans
Attorney, Agent, or Firm—Krass & Young

[57] ABSTRACT

Perchloroethylene is oxychlorinated to provide hexachloroethane which is reacted with methane to produce methyl chloride which is hydrolyzed to form methyl alcohol product and hydrogen chloride which is recycled to the oxychlorination step.

8 Claims, 1 Drawing Sheet

METHYL ALCOHOL PROCESS

REFERENCES TO RELATED APPLICATIONS

This application is a continuation-in-part of copending application Ser. No. 297,298 filed Jan. 13, 1989, which in turn is a continuation-in-part of application Ser. No. 040,839 filed Apr. 20, 1987, which is a continuation-in-part of application Ser. No. 793,534 filed Oct. 31, 1985. The latter two applications, namely Ser. No. 040,839 and Serial No. 793,534, are now abandoned.

FIELD OF THE INVENTION

This invention relates to a novel method of producing methyl alcohol (methanol) from methane using three reaction steps operated in tandem. Beginning with the first step, perchloroethylene ($CCl_2CCl_2$) is oxychlorinated with hydrogen chloride and oxygen to obtain hexachloroethane ($CCl_3CCl_3$). In the second step methane is chlorinated with hexachloroethane to produce methyl chloride, hydrogen chloride and regenerated perchloroethylene. The methyl chloride from the second step is isolated and hydrolyzed with water in the third step to give methyl alcohol and hydrogen chloride. The reactions are operated in a balanced mode by recycling perchloroethylene from the second step to the first step, and by recycling hydrogen chloride produced in each of the second and third steps to the first step. The process has the distinct advantage of providing high yields and offering significant cost savings over existing technology.

BACKGROUND OF THE INVENTION

Description of the Prior Art

The conventional method of producing methyl alcohol is to pass synthesis gas containing carbon monoxide and hydrogen over a catalyst at high temperatures and pressures. The temperature of the reaction is maintained at about 300° C. Because of the unfavorable equilibrium, the reaction must be carried out at high pressures, from about 3,000 to 5,000 psi. Even under these conditions only a fraction of the synthesis gas is converted to methanol in each pass and therefore it must be recycled to the reactor after condensing the methyl alcohol which is formed.

There are two principal sources of synthesis gas. Coal may be reacted with steam at elevated temperatures to produce a gas containing carbon monoxide and hydrogen. After purification and fortification with additional hydrogen, the gas is suitable for methanol synthesis. Alternatively, synthesis gas can be produced from methane by partial oxidation or by the reaction with carbon dioxide.

In order to overcome the limitations of existing methods of producing methyl alcohol, proposals have been made to convert methane directly to methyl alcohol via partial oxidation. On paper this approach would appear to be extremely attractive. Only one carbon-hydrogen bond of the methane molecule would be broken in this reaction, thus promising a greatly simplified procedure. Unfortunately, all attempts at the direct synthesis of methyl alcohol from methane have failed. The right catalyst or combination of conditions has yet to be discovered.

It is therefore an object of the present invention to provide a process for the production of methyl alcohol from methane that overcomes the disadvantages of the conventional methods. Another object is to produce methyl alcohol in high yields from methane. Still a further object is to avoid the necessity of operating a process at high pressure which requires specialized and expensive apparatus.

SUMMARY AND DETAIL DESCRIPTION

Figure 1:
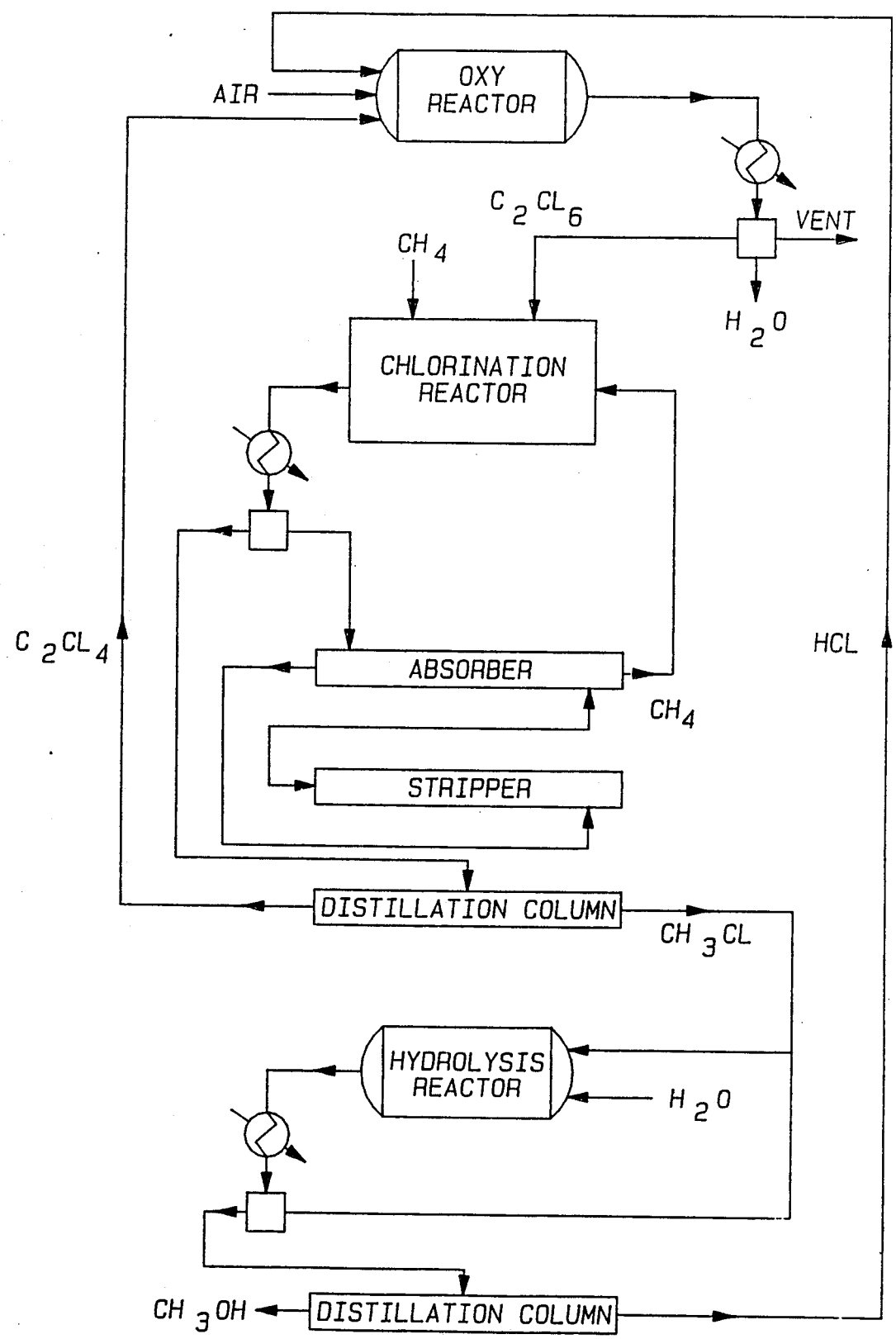
FIG. 1 is a diagrammatic representation of a preferred means for operating the present invention. It shows the oxychlorination reactor, the chlorination reactor, and the hydrolysis reactor as well as means for separating perchloroethylene and hydrogen chloride and recycling these streams back to the oxychlorination reactor.

The invention in a preferred embodiment comprises a process for the production of methyl alcohol from methane whereby methane is chlorinated to methyl chloride using hydrogen chloride as the indirect source of chlorine, and methyl chloride is subsequently hydrolyzed to methyl alcohol. The process is conducted so that there is no net requirement of chlorine or hydrogen chloride. To achieve these results, three reaction steps are operated in tandem so that the products or by-products from one step become the reactants for another step.

For the purpose of this description, the first reaction step is identified as the oxychlorination of perchloroethylene with hydrogen chloride and oxygen or air in the presence of an oxychlorination catalyst to give hexachloroethane and water. The hexachloroethane from the first reaction step is reacted with methane feedstock in the second reaction step to produce predominantly methyl chloride, perchloroethylene and hydrogen chloride. The perchloroethylene and hydrogen chloride so produced are separated from the reaction products and recycled to the first reaction step. The methyl chloride is fed to the third reaction step where it is hydrolyzed with water or steam to form methyl alcohol and hydrogen chloride. The hydrogen chloride is separated from the methyl alcohol product and recycled to the first reaction step.

The chemical reactions which take place in different steps of the process can be illustrated by the following equations:

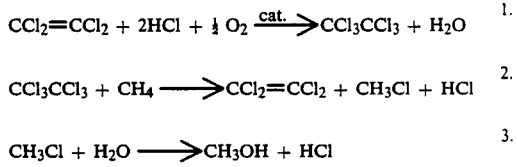

By combining equations 1, 2 and 3 one obtains the following equation which represents the overall reaction:

The first reaction, in which perchloroethylene is oxychlorinated to hexachloroethane employing an oxychlorination catalyst, may typically be carried out in a molten salt reactor, fluidized bed reactor, or in a shell and tube reactor. By the means of such reactor designs the temperature is maintained preferably in the range from about 200° C. to about 375° C. The catalyst of choice is copper chloride contained in a molten salt or deposited on an inert support. This is the well-known Deacon catalyst which has been used in experimental processes to produce chlorine from hydrogen chloride and air. Various salts may be admixed with copper chloride to promote its effectiveness, e.g., potassium chloride, ferric chloride, and lead chloride.

The second reaction typically is conducted in the vapor phase at an elevated temperature preferably in the range from about 400° C. to about 700° C. The probable mechanism by which methane is chlorinated is a series of free-radical reactions. Normally higher chlorinated methane including methylene chloride, chloroform and carbon tetrachloride would be produced along with methyl chloride. In the present invention, however, the formation of these higher chlorinated compounds is suppressed by using an excess of methane and by approximating plug flow conditions in the chlorination reactor. Careful control over temperature and residence time is also important.

As a feature of the invention, temperature control of the second reaction step is facilitated using hexachloroethane instead of chlorine as the chlorinating agent. Substitution chlorination, such as the formation of methyl chloride from methane and chlorine, releases considerable heat. By contrast, dissociation reactions, such as the instant decomposition of hexachloroethane to perchloroethylene and chlorine, absorb a substantial quantity of heat. Thus, according to the present invention, when these two reactions, substitution chlorination and dissociation, are conducted in an intimate manner, the heat requirements can be closely balanced.

Methyl chloride from the second reaction step is fed to the hydrolysis reactor where it is hydrolyzed with water or steam in the third reaction step to produce methyl alcohol and hydrogen chloride. Although it would be possible to feed a stream of methane containing methyl chloride to the hydrolysis reactor, the simplest procedure is to separate methyl chloride from unreacted methane beforehand. The methyl chloride can be scrubbed from the methane by absorption in a refrigerated stream of perchloroethylene. The separated methane is recycled to the chlorination reactor.

The net free energy change associated with the hydrolysis reaction indicates that the equilibrium favors the reverse reaction at ambient temperatures. In order to improve the equilibrium conditions, the hydrolysis reaction can be carried out at elevated temperatures. To further increase the yield of methyl alcohol, an excess of water or steam is used. A catalyst as alumina gel is employed in the reverse reaction and therefore is recommended for the hydrolysis reaction.

The effluent from the hydrolysis reactor is cooled in order to condense the methanol and hydrochloric acid. Unreacted methyl chloride is separated from the condensate and recycled back to the hydrolysis reactor. Likewise, any dimethyl ether that may be formed can be recycled. The condensate is fractionated to separate the hydrogen chloride for recycling to the oxychlorination reactor. The methyl alcohol is further purified and dried for commercial use.

For successful operation of the process, additional details should be noted. Strict adherence to the following rules will avoid unnecessary difficulties:

1. Hexachloroethane produced via oxychlorination must be isolated from the reaction products before being fed to the thermal chlorination reactor. Any impurities, with the exception of perchloroethylene or pentachloroethane, must be separated from the hexachloroethane in order to avoid the formation of byproducts. The chlorination reactor must be kept under anhydrous conditions or above the dew point so as to prevent severe corrosion problems. All oxygen has to be excluded from the chlorination reactor to avoid burning and to prevent the formation of water.

2. Hydrogen chloride, before being recycled to the oxychlorination reactor, must be free of all hydrocarbons to prevent combustion reactions and to avoid pollution problems caused by the release of hydrocarbons in the vent gases.

3. Perchloroethylene that is reformed in the chlorination reactor must be isolated from the product stream before being recycled to the oxychlorination reactor. Any saturated hydrocarbons which are fed to the oxychlorination reactor will be subject to burning. Unsaturated hydrocarbons, other than perchloroethylene, will be chlorinated in the oxychlorination reactor and eventually lead to unwanted byproducts. Any volatile impurities will escape in the vent gases.

4. Methane that is recycled to the chlorination reactor must be dried in order to avoid potential corrosion problems.

The required separation of the recycle streams cannot be taken for granted. For example, hexachloroethane is very slightly miscible in water and thus presents a challenge in drying it completely. The principles of azeotropic distillation are used to separate hydrogen chloride. And finally, allowances must be made for the formation of any higher chlorinated methane compounds that may be condensed with the reformed perchloroethylene.

Methyl alcohol produced by the methods of the present invention is a valuable item of commerce. Substantial quantities of methyl alcohol are converted to formaldehyde which is a component of several plastics. Methyl alcohol shows promise as a general motor fuel. Widespread use of methyl alcohol in internal combustion engines would reduce air pollution caused by the emission of exhaust fumes. Such improvements can be gained without significantly impairing engine performance.

The embodiments of the present invention in which exclusive property or privilege is claimed are defined as follows:

1. A process for the production of methyl alcohol from methane comprising the following steps operated in tandem;

first, subjecting perchloroethylene to oxychlorination with hydrogen chloride and oxygen in the presence of an oxychlorination catalyst to give reaction products consisting essentially of hexachloroethane and water;

second, isolating said hexachloroethane from the reaction products of the first step and reacting it with methane feedstock in the vapor phase to produce predominantly methyl chloride, perchloroethylene and hydrogen chloride, separating said perchloroethylene and hydrogen chloride from the reaction products and recycling the perchloroethylene and hydrogen chloride thus separated to the first step; and third, subjecting the methyl chloride from the second step to hydrolysis with water to produce methyl alcohol and hydrogen chloride, separating said methyl alcohol and hydrogen chloride from the reaction products, and recycling the hydrogen chloride to the first step.

2. A process according to claim 1 in which the source of oxygen for the first step is air.

3. A process according to claim 1 in which the catalyst used in step 1 comprises copper chloride.

4. A process according to claim 3 where the catalyst comprises an admixture of copper chloride with a salt selected from the group consisting of potassium chloride, ferric chloride, and lead chloride.

5. A process according to claim 1 in which the oxychlorination reaction with perchloroethylene is carried out at a temperature in the range from about 200° C. to about 375° C.

6. A process according to claim 1 in which the vapor phase reaction is carried out at a temperature in the range from about 400° C. to about 700° C.

7. A process according to claim 1 in which the hydrolysis reaction of step 3 is carried out in the presence of a catalyst.

8. A process according to claim 7 in which the catalyst comprises alumina gel.

* * * * *